US00PP16455P3

(12) United States Plant Patent
Kaagman

(10) Patent No.: US PP16,455 P3
(45) Date of Patent: Apr. 18, 2006

(54) ***OSTEOSPERMUM* PLANT NAMED 'OSTE PINKBIC'**

(50) Latin Name: *Osteospermum ecklonis*
Varietal Denomination: Oste Pinkbic

(75) Inventor: Pim Kaagman, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 138 days.

(21) Appl. No.: 10/885,564

(22) Filed: Jul. 6, 2004

(65) Prior Publication Data

US 2006/0010546 P1 Jan. 12, 2006

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Jondle & Associates P.C.

(57) ABSTRACT

An *Osteospermum* cultivar particularly distinguished by pink bi-colored inflorescences, dark green foliage and vigorous growth.

1 Drawing Sheet

Genus and species: *Osteospermum ecklonis.*
Variety denomination: 'Oste Pinkbic'.

BACKGROUND OF THE NEW PLANT

The variety 'Oste Pinkbic' originated from a cross made in October, 2000. The female parent is a light violet proprietary line OX-48 (unpatented). The male parent is 'Seaside', (patent status unknown) which is a light pink bi-color commercial variety. Seed from this cross was sown in June 2001. In October 2001, single-plant selections were made for vegetative propagation using plant habit and inflorescence color as selection criteria. One selection became the new variety 'Oste Pinkbic'.

'Oste Pinkbic' is a product of a planned breeding program intended to create new *Osteospermum* cultivars with pink bi-colored inflorescences, dark green foliage, and vigorous growth.

The new cultivar was created in 2000 in Gilroy, Calif. and has been asexually reproduced repeatedly by vegetative cuttings and tissue culture in Gilroy, Calif.; and Andijk, The Netherlands over a two ½ year period. The plant has also been trialed at Gilroy, Calif.; and Andijk, The Netherlands. The present invention has been found to reproduce true to type in successive generations of asexual reproduction.

DESCRIPTION OF PHOTOGRAPH

This new *Osteospermum* plant is illustrated by the accompanying photograph which shows blooms, buds, and foliage of the plant in full color, the colors shown being as true as can be reasonably obtained by conventional photographic procedures. Photographs were taken from plants grown in The Netherlands in the late winter/spring in a 54° Fahrenheit greenhouse. Plants are 4½ months old, had one terminal pinch at 3 weeks old, and are grown in a 4 inch pot with 3 treatments of CYCOCEL.

The photograph shows the mature plant with an inset photograph of a close-up of the inflorescence.

DESCRIPTION OF THE NEW CULTIVAR

The following detailed descriptions set forth the distinctive characteristics of 'Oste Pinkbic'. The data, which defines these characteristics, were collected from asexual reproductions carried out in Gilroy, Calif. The plant history was taken on 5 month old plants grown in one gallon pots in the late winter/spring season, in a LEXAN covered greenhouse under natural light and color readings were taken in the greenhouse under natural lights. Color references are primarily to The R.H.S. Colour Chart of The Royal Horticultural Society of London (R.H.S.) 2001. Texture description details were observed under a dissecting microscope according to The New Royal Horticultural Society Dictionary of Gardening (1992).

THE PLANT

Classification: *Osteospermum ecklonis.*
Botanical: *Osteospermum.*
Commercial: 'Oste Pinkbic'.
Form: Upright, nicely compact and mounded.
Growth and branching habit: Good vigorous, freely branched habit.
Height: From soil level to top of blooms: Approximately 20–24 cm.
Width: Approximately 20–30 cm.
Time to produce a finished flowering plant: 8–11 weeks for a 6 inch pot.
Outdoor plant performance: Herbaceous, frost tender perennial patio planters, mixed container plantings or garden beds.
Time to initiate and develop roots: Approximately 8–14 days in the greenhouse.
Root description: Fibrous, white.

THE LEAVES

Leaf arrangement: Alternate.
Fully expanded, length: 5.0–6.4 cm; Width: 3.5–4.0 cm.

Leaf shape: Obovate.
Leaf margin: Dentate.
Apex aspect: Broadly acute.
Base aspect: Acuminate.
Leaf color: Upper surface — RHS 147A (yellow-green); Under surface RHS 137A (green).
Leaf texture: Pilose.
Venation: Pinnate.
Venation color: RHS 144A (yellow-green).
Petiole length: 2.0–3.0 cm.
Petiole diameter: 0.4–0.5 cm.
Petiole color: RHS 144A (yellow-green).
Petiole texture: Hirsute.

THE STEM

Length: 18–20 cm.
Diameter: 0.4–0.5 cm.
Stem internode length: 1.0–1.2 cm.
Color: RHS 144A (yellow-green).
Texture: Pilose.
Stem anthocyanin: None.
Peduncle color: RHS 144B (yellow-green).
Peduncle length: 7.0–9.0 cm.
Peduncle diameter: 0.2 cm.
Peduncle texture: Pilose and glandular hairs.

THE BUD

Shape: Ovate.
Diameter: 0.6–0.9 cm.
Length: 1.0–1.3 cm.
Color at tight bud (starting to show color): RHS 161A (greyed-yellow).

THE FLOWER

Blooming habit: Plants flower freely from the spring through fall given the proper growing conditions.
Longevity of individual blooms on the plant: 7–14 days.
Fragrance: None.
Inflorescence type: Terminal and axillary inflorescences held above the foliage. Capitulum inflorescence, radially symmetrical.
Inflorescence diameter: 5.5–6.0 cm.
Inflorescence depth: 1.4–1.5 cm.
Disc diameter: 1.1–1.2 cm.
Ray floret, immature color: Upper surface is RHS N155B (white); between RHS 75A and RHS 75B (light purple) at the outer two-thirds portion of the florets, shading into the middle portion of florets and light shade of RHS 75A (light purple) in longitudinal stripes; basal portion of florets RHS 75B (light purple); middle portion RHS N155B (white) and RHS 69D (pink). Under surface is RHS 75C (light purple); with longitudinal stripes of shades of RHS 176B (greyed orange) and shading of RHS 83D (violet) at the apex; shading of RHS 182D (greyed red) in between the stripes. Mature Color: Upper surface is RHS N155B (white); between shades of RHS 72C and RHS 72D (light purple) on the outer two thirds with RHS 75C (light purple) longitudinal stripes; basal shading of RHS 72D (light purple) middle portion shading of RHS N155B (white) and RHS 69D (pink). Under surface is RHS 75C (light purple) with longitudinal stripes of shades of RHS 176B (greyed orange) and shading of RHS 83D (violet) at the apex; shading of RHS 182D (greyed-red) in between the stripes.
Ray floret length: 2.9–3.1 cm.
Ray floret width: 0.8–0.9 cm.
Ray floret apex shape: Emarginate to Praemorse.
Ray floret base shape: Cuneate.
Ray floret margin: Entire.
Ray floret texture: Papillose and hirsute on the basal margins.
Ray floret quantity: Approximately 19.
Ray floret shape: Oblanceolate.
Disc floret, tube color: RHS 73C (red-purple) with RHS N77A (light purple) tip.
Shape: Tubular, elongated.
Length: 0.5–0.6 cm.
Diameter at apex: 0.1–0.2 cm.
Apex shape: 5-pointed, acute.
Apex color: RHS N77A (purple).
Disc floret quantity: Approximately 70–75.
Phyllaries, color:
*Upper surface.*—RHS 138A.
*Lower surface.*—RHS 137D.
Length: 0.9–1.2 cm.
Width: 0.1 cm.
Base: Fused.
Margin: Entire.
Shape: Linear.
Apex: Acute.
Texture: Hirsute and glandular hairs.

THE REPRODUCTIVE ORGANS

Androecium, pollen color: RHS 23A (yellow-orange).
*Filament color.*—RHS N155D (white).
*Location.*—On disc florets.
Gynoecium, pistil: 1 per floret.
*Pistil length.*—0.5 cm.
*Location.*—On disc and ray florets.
*Stigma color.*—RHS N77A (purple).
*Style color.*—RHS 73C (light purple).
*Fruit seed set.*—Has not been observed.

DISEASE AND INSECT RESISTANCE

Has not been observed.

COMPARISON WITH KNOWN CULTIVARS

'Oste Pinkbic' differs from the female parent, OX-48 in the following ways: 'Oste Pinkbic' is later to flower, more vigorous, has larger inflorescences and has a lighter inflorescence color than OX-48.

'Oste Pinkbic' differs from the male parent, 'Seaside' in the following ways: 'Oste Pinkbic' is earlier to flower, has a lighter inflorescence color, better branching and has shorter peduncles than 'Seaside'.

I claim:

1. A new and distinct cultivar of *Osteospermum* plant as shown and described herein.

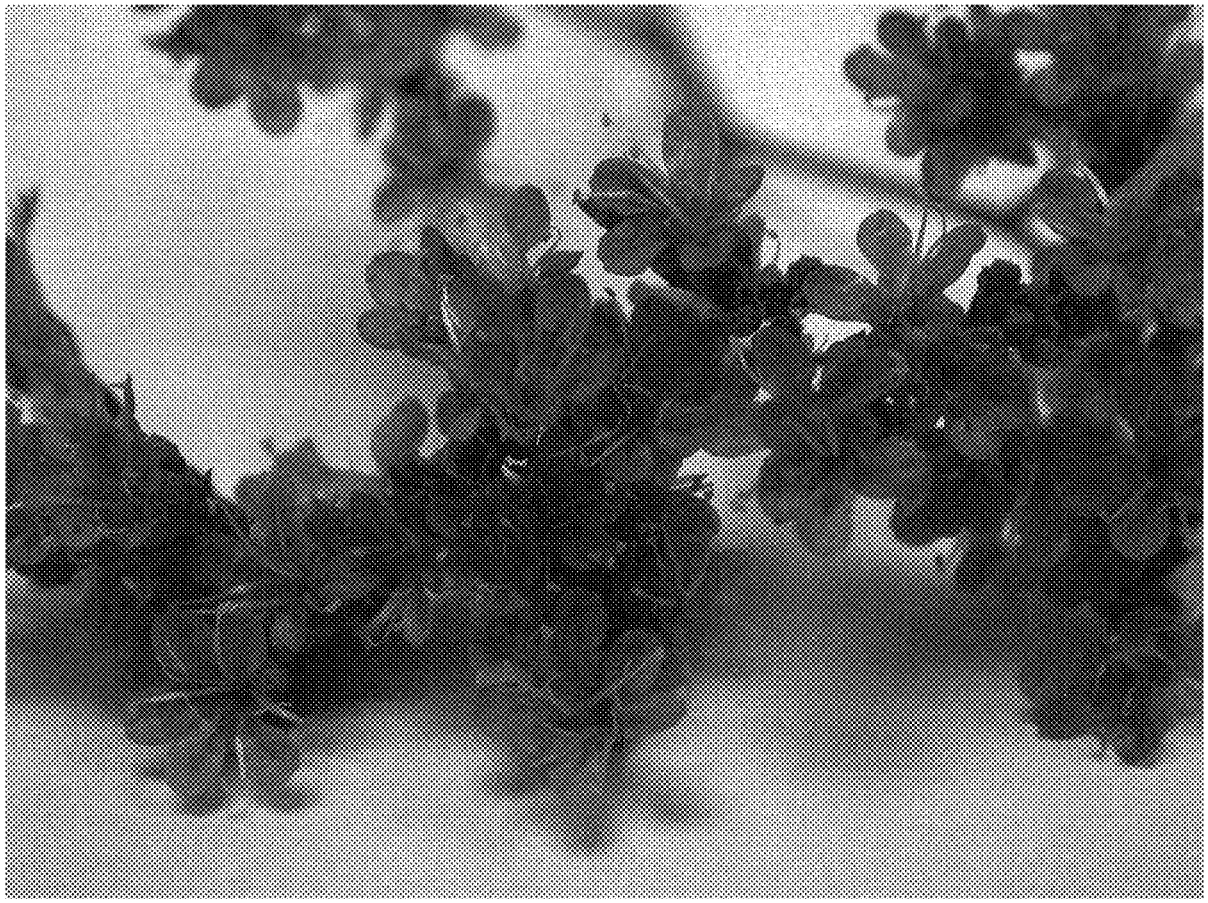

* * * * *